United States Patent
Cruitt et al.

(10) Patent No.: US 6,934,220 B1
(45) Date of Patent: Aug. 23, 2005

(54) PORTABLE PROGRAMMABLE MEDICAL ALERT DEVICE

(75) Inventors: Stanley L. Cruitt, Winston-Salem, NC (US); Sidney Chan, Vancouver (CA); Jaroslav V. Tichy, Delta (CA)

(73) Assignee: ALR Technologies, Inc., Winston-Salem, NC (US)

( * ) Notice: Subject to any disclaimer, the term of this patent is extended or adjusted under 35 U.S.C. 154(b) by 163 days.

(21) Appl. No.: 10/462,096

(22) Filed: Jun. 13, 2003

Related U.S. Application Data (60) Provisional application No. 60/388,264, filed on Jun. 13, 2002.

(51) Int. Cl.$^7$ .............................................. G04B 47/00
(52) U.S. Cl. .............................. 368/10; 368/72; 368/73; 368/74; 368/250; 368/251; 368/247
(58) Field of Search .............................. 368/72–74, 247, 368/250, 251, 10

(56) References Cited

U.S. PATENT DOCUMENTS

| | | | | |
|---|---|---|---|---|
| 4,095,213 A | * | 6/1978 | Hayden | 340/644 |
| 4,258,354 A | * | 3/1981 | Carmon et al. | 340/309.4 |
| 4,390,289 A | * | 6/1983 | Houlihan | 368/286 |
| 4,432,652 A | * | 2/1984 | Munekata et al. | 368/69 |
| 4,589,779 A | * | 5/1986 | Hatta et al. | 368/74 |
| 4,912,688 A | * | 3/1990 | Syfert | 368/67 |
| 4,920,525 A | * | 4/1990 | Meister | 368/250 |
| 5,089,998 A | * | 2/1992 | Rund | 368/72 |
| 5,289,157 A | * | 2/1994 | Rudick et al. | 340/309.7 |
| 5,365,494 A | * | 11/1994 | Lynch | 368/10 |
| 5,666,331 A | * | 9/1997 | Kollin | 368/245 |
| 6,075,755 A | * | 6/2000 | Zarchan | 368/10 |
| 6,421,650 B1 | * | 7/2002 | Goetz et al. | 705/3 |

\* cited by examiner

*Primary Examiner*—Andrew H. Hirshfeld
*Assistant Examiner*—Andrea H. Evans
(74) *Attorney, Agent, or Firm*—Robert W Pitts

(57) ABSTRACT

A portable programmable medical alert device can be used to program multiple events, each of which will be signaled by an audible and a visual alarm. The user can program and reprogram medication schedules using only the portable alert device. The device, including a battery powered microcontroller, can be programmed by manipulation of two input switches, a push button switch and a two position to prevent inadvertent programming. Each programmed event will be signaled at the same time of day at which the alarm was originally set. When the alarms are transmitted to a user, the alert or reminder can be acknowledged by pressing the push button switch. The user can also activate the device prior to the next scheduled alarm without affecting subsequent alarms or alerts. Outputs can be audible and/or visible outputs, including an LCD. Inputs can be alternatively programmed by computer.

12 Claims, 8 Drawing Sheets

PORTABLE PROGRAMMABLE MEDICAL ALERT DEVICE

CROSS REFERENCE TO PRIOR CO-PENDING APPLICATION

This application claims benefit of prior co-pending Provisional Patent Application Ser. No. 60/388,264 filed Jun. 13, 2002.

BACKGROUND OF THE INVENTION

1. Field of the Invention

This invention is related to a portable device that can be programmed and actuated by a user to alert the user in accordance with a medication schedule or at the time when a similar, regularly scheduled, medical procedure or treatment is required. This device is adapted for use by a patient or other person who is not medically trained. The device can be used to alert the user to multiple daily events.

2. Description of the Prior Art

Monthly reminder devices, suitable for use in reminding pet owners of monthly medications for use in heartworm prevention and flea and tick control are shown in U.S. Design Pat. 446,739; U.S. Design Pat. 446,740; and U.S. Design Pat. 447,074. These devices are normally programmed by a veterinarian who supplies the device with the appropriate medication. To program these devices, the user presses and holds a button on the bottom front of the device on a selected day and time of day, normally the day and time on which the medication is prescribed. The user continues to press the button until a two tone sound is heard and the button is then released. Two seconds after releasing the button, a reminder alarm will sound. The button should then be pressed and released to silence the alarm. The unit will then emit four beeps. The unit is then programmed and the reminder alarm will sound every thirty days from the date and time on which the push button was activated. When the alarm sounds, a pet owner can then press the push button to silence the alarm. To de-program the unit, the pet owner or veterinarian should push the button and the unit will beep, after which the user will continue to hold the button until the unit emits a two tone sound. The button can then be released and the unit is deprogrammed.

The user can press the button at any time during the thirty day interval, and the unit will respond with a number of beeps equal to the number of weeks until the next scheduled alarm. When the scheduled event takes place, the alarm will sound for one minute and will go silent for five minutes, after which the alarm will again sound for one minute. This sequence will continue until the user presses the push button to deactivate the alarm. While a unit is silent during an alarm, a light on the front face will continue to flash. If the button is pushed during this silent period, an audible alarm will sound. The button can then be pressed and released to silence the alarm. During the thirty day period between reminder alarms, the light will flash every ten minutes.

These devices are battery powered and can be magnetically held on a refrigerator or other suitable location. The device includes a programmable microcontroller with memory mounted on an internal printed circuit board with switch contacts an LED and an audible output device. Similar devices can be programmed to alarm weekly.

Although these simple devices are suitable for alerting pet owners to administer scheduled medications on relatively long intervals, they lack the flexibility to remind humans to administer multiple medications on more frequent and often-times schedules which are frequently altered. For instance these devices are not suitable for providing multiple daily reminders. These devices also do not permit deactivation of an alarm if the user should administer a medication or perform a medical procedure prior to the time that the alarm sounds. The alarm also cannot be deactivated when an audible alarm would interrupt some other activity. These devices are also not suitable for portable use. A user cannot put one of these devices in a pocket, because the push button can be inadvertently actuated.

Other prior art reminder devices are know. However, most of these prior art devices must be programmed by a skilled technician or require specialized equipment, to program multiple daily events into a portable device. Even when alternative embodiments are used in which the device is remotely programmed, for example by a computer or over the Internet or telephone line, the simple user execution steps and interaction for the instant invention will remain substantially the same.

SUMMARY OF THE INVENTION

A programmable reminder device according to this invention is used to provide at least one daily reminder to a user. The device includes a microcontroller executing time keeping and other functions. A signaling component is responsive to the microcontroller to emit a signal detectable by the operator of the reminder device. The basic device also includes first and second switch inputs. The microcontroller is configured so that simultaneous actuation of both switch inputs sets the microcontroller to activate the signaling component daily at the same time that the two switch inputs were originally simultaneously actuated. A device of this type is especially suitable for use as a programmable medication reminder in which the microcontroller would include a clock and memory. The first input switch and the second input switch are connected to the microcontroller so that when the first input switch is activated while the second input switch is in an activated state at a specific time of day, that time of day will be stored in the memory as an event and the microcontroller will send a signal to activate the output device at the same time on succeeding days; and the first input switch and the second input switch could also be operated so that when the second input switch is deactivated, while the first input switch is in an activated position, the microcontroller will not activate the output device upon a next event.

The preferred embodiment of this device comprises a portable battery powered medical alert device for reminding a user of a scheduled medical procedure. The microcontroller is powered by a battery, and has input ports comprising means for receiving programming inputs and for receiving execution inputs, and output ports. The output device is connected to the output ports and to emit a signal detectable by a the user upon the occurrence of a scheduled medical procedure and for signaling the user upon receipt of programming inputs. The microcontroller can be manually or automatically switched between an armed state and a disarmed state. A single push button switch is connected to the microcontroller for inputing programming inputs to the microcontroller when the microcontroller is in the armed state and for inputting execution inputs when the microcontroller is in the disarmed state.

The audible output device on this portable, daily medical reminder device can be deactivated so that the audible output device will not respond at the next scheduled time of day, but will respond at each subsequent time of day for the day on which the audible output device is deactivated and for all subsequent days. The user can thus deactivate the audible output device to prevent disruption or if the scheduled medical procedure is preformed prior to the scheduled time of day.

DETAILED DESCRIPTION OF THE PREFERRED EMBODIMENTS

FIGS. 1 through 6 show a basic portable, programmable medical alert device or unit 10 in accordance with this invention. The height of this device 10 is approximately sixty (60) mm with a depth of approximately sixteen (16) mm and its maximum width is approximately forty six (46) mm. This size makes the medical reminder device 10 suitable for use on a key ring or in a pocket or purse. The device housing includes a housing cover 34 secured to a housing base 32 by a pair of screws, not shown. The active components of the device are located within this housing.

Figures 1, 4:
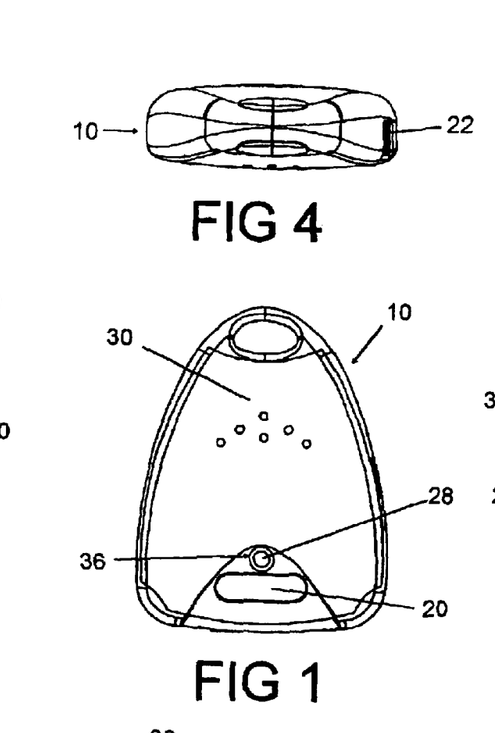
FIG. 1 is a front view of a medical alert device in accordance with this invention.
FIG. 4 is a top view of the device of FIG. 1.
Figure 2:
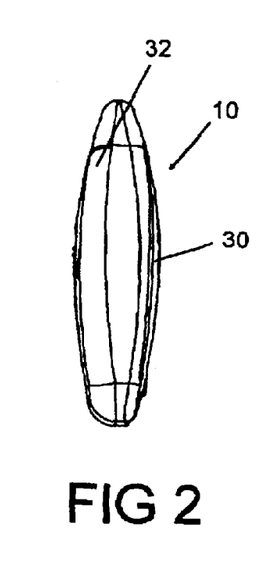
FIG. 2 is a left side view of the device of FIG. 1.
Figure 7:
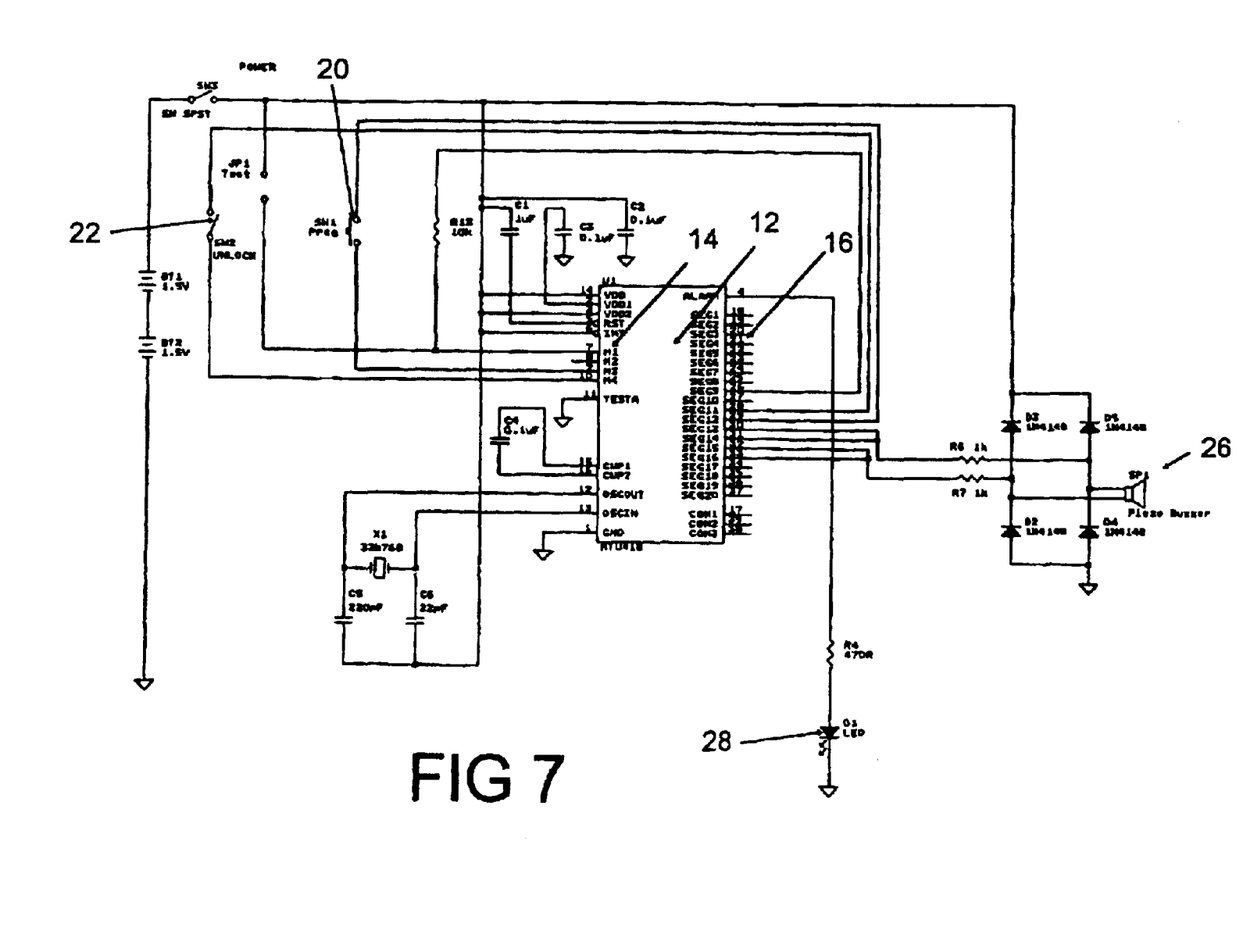
FIG. 7 is a schematic of one circuit implementing this invention.
Figure 8:
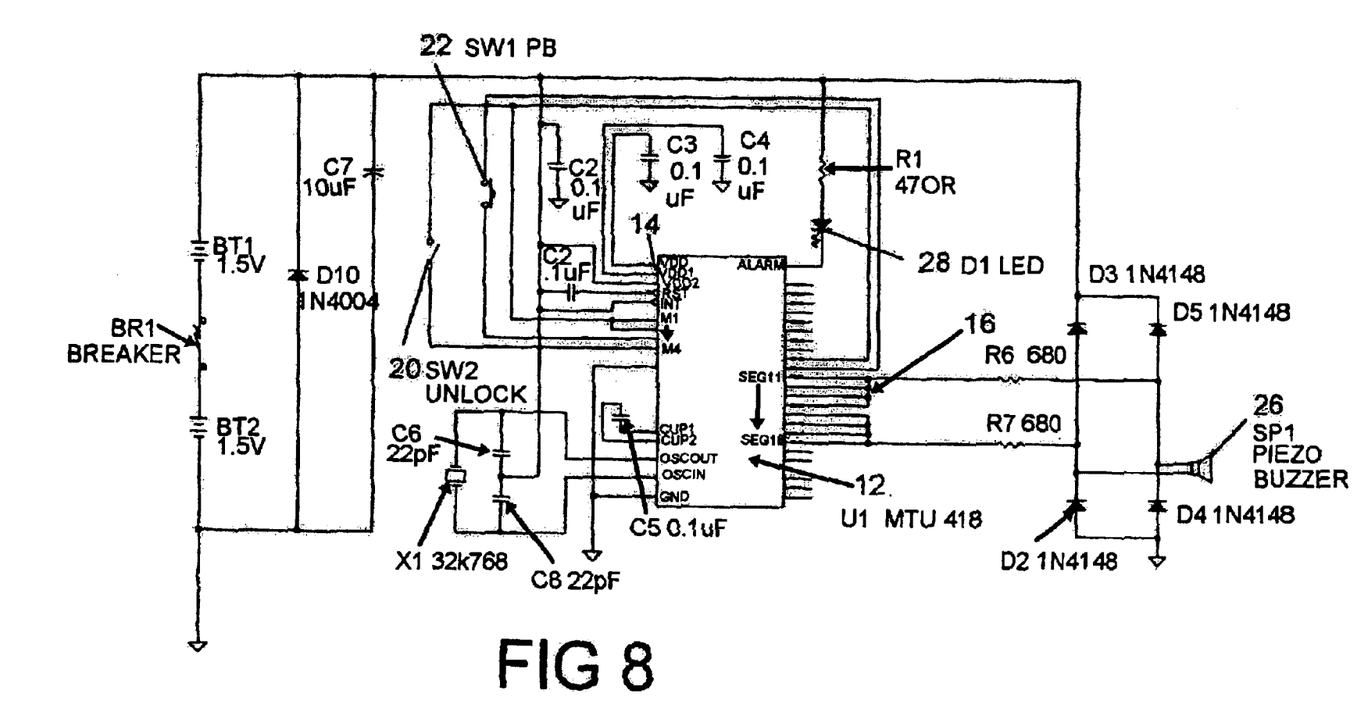
FIG. 8 is a schematic of another circuit implement this invention.

As seen in FIG. 1, the device includes a push button switch 20 on its front face. An opening 36 for a light emitting diode 28 is located immediately above the push button switch 20. A series of smaller openings on the front face are positioned so that sounds emitted by an alarm or output device 26, located on the interior of the unit, will be audible. An elliptical opening at the top of the device is suitable for receipt of a key ring. The housing base 32 also includes an opening 40 on its right side through which a printed circuit board mounted slide switch 22 protrudes. This slide switch 22 can only be moved between a set and a lock position by the application of an external force, so that this switch 22 can be said to have two stable positions. The push button switch 20 on the front of the unit can be activated by an external force closing the switch, but when that external force is removed, the push button switch will return to its open position. The push button switch 22 can therefore be inadvertently activated, and cannot be solely relied upon for programming the portable reminder device or for providing execution inputs, such as acknowledging an alarm or alert signal. Push button switch 22 comprises a switch input and in turn is part of a means for inputing programming inputs to the microcontroller when the microcontroller is in the armed state and for inputting execution inputs when the microcontroller is in the disarmed state FIGS. 7 and 8 are alternative schematics of circuits that can be employed to implement this invention in its basic form. The components forming each circuit can be mounted on a printed circuit board, which is mounted on the interior of the housing formed by mating the housing cover 30 to the housing base 32. In these preferred embodiments, the circuits employ a 4-bit microcontroller 12, which can be a MTU418 microcontroller available from Myson Technology. Other microcontrollers can also be employed. This microcontroller includes input ports 14, designated by the manufacturer as ports M1–M4. to which the switches 20, 22 can be connected. These input ports are capable of preventing ON/OFF chattering of a signal, which detects a change of the switch signal. Output devices 26 and 28 can be connected to output ports 16, designated by the manufacturer as DC output ports SEG 11–19 and ALARM. In each embodiment an LED 28, which serves as the visual output device, is connected to the ALARM output port. The other output ports 16 are connected to a piezoelectric buzzer, which comprises the primary or audible output device 26. SW1, designated on the schematics as a programming switch, is the push button switch or first input switch 20, which comprises a conventional printed circuit board push button switch. SW2, designated on the schematics as an unlock switch, is the slide or two position switch 22, which is also mounted on a printed circuit board. Power is provided by two 1.5 volt batteries 24 is series. These batteries are connected to the microcontroller 12 in a conventional manner.

The clock oscillation circuitry is formed by connecting a 32768 Hz quartz crystal to the clock pin OSCIN and OSCOUT, and an oscillation frequency adjusting timer capacitor to OSCIN. The clock oscillation circuitry is conventional and provides both timing for the microcontroller and the time of day and elapsed time for the medical alert device 10 can be derived therefrom.

This microcontroller 12 also has a halt function to minimize current dissipation. In the halt mode, the microcontroller does not execute the program which resides in the ROM memory. Only the oscillator circuit, predivider and timer are in operation. This microcontroller provides several means for entering and exiting the halt state. Typical values of components, such as capacitors, resistors and diodes, are noted on these schematics.

Figure 9:
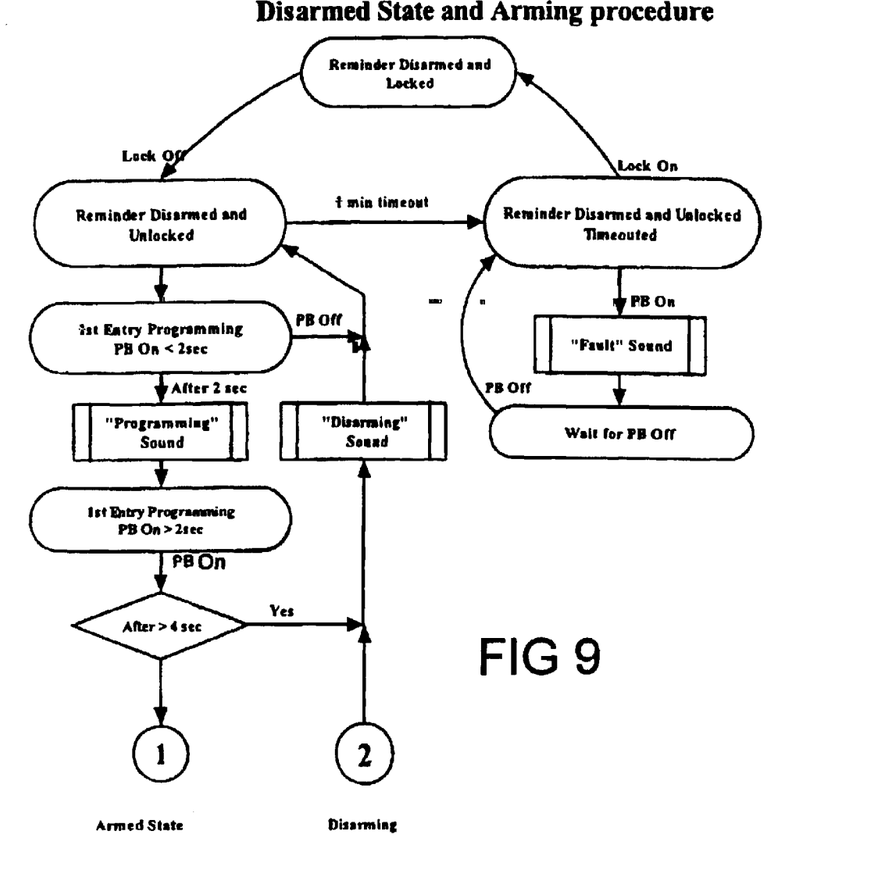
FIG. 9 is a flow chart showing the steps necessary to program a first alert into a microcontroller.
Figure 10:
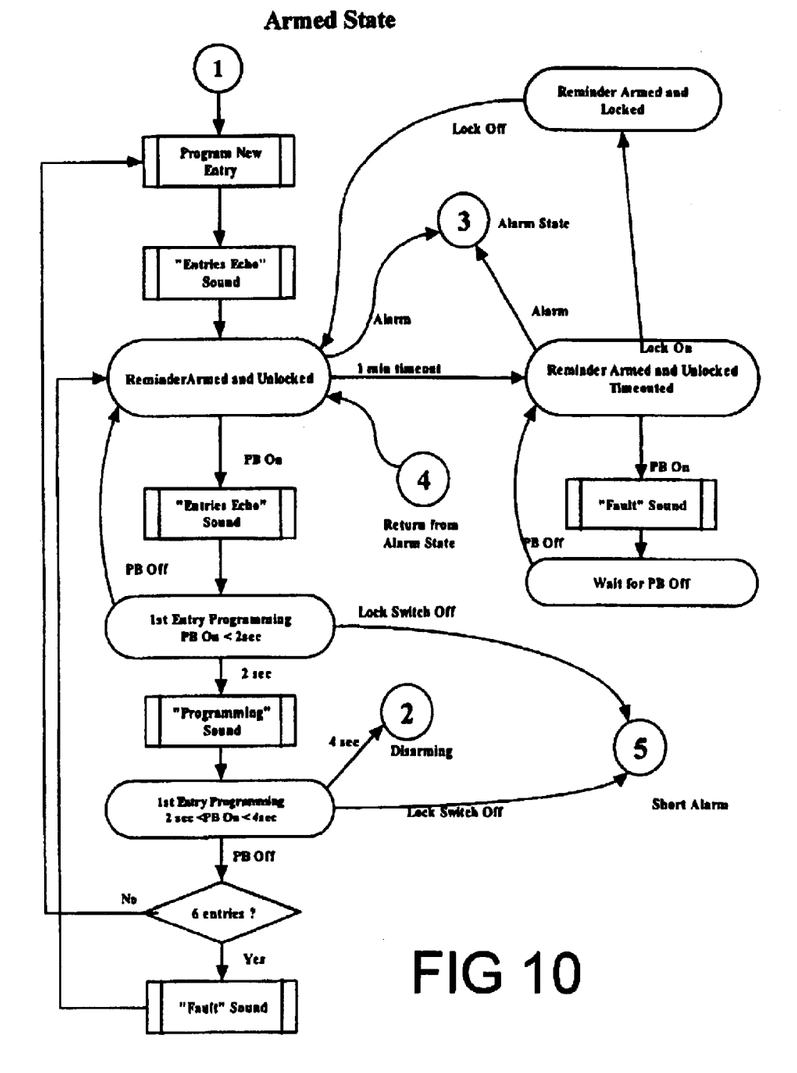
FIG. 10 is a flow chart showing the armed state of the reminder unit including the manner in which additional alerts are programmed into a microcontroller.
Figure 11:
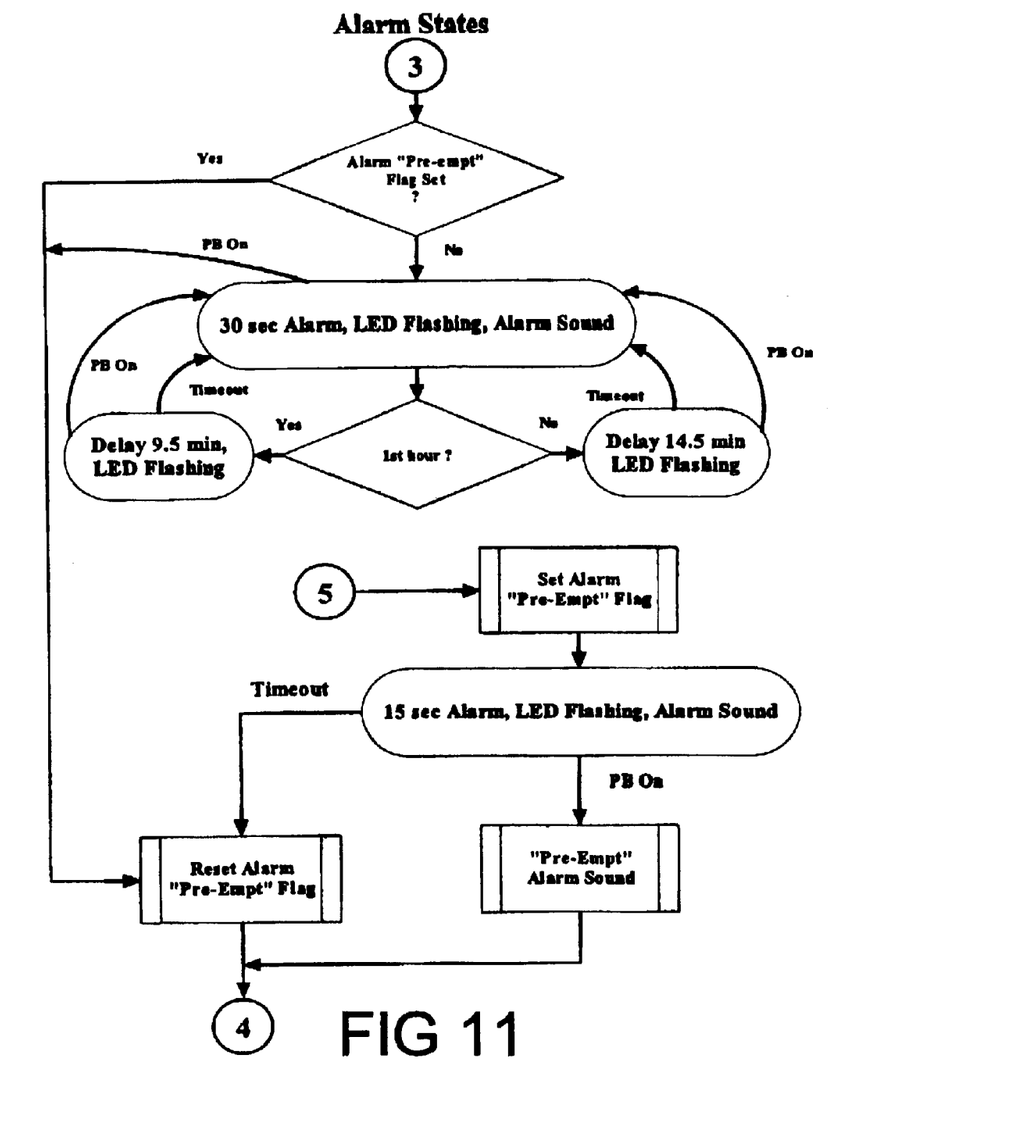
FIG. 11 is flow chart showing the medical reminder alarm states.

This microcontroller includes memory for storing software or firmware for implementing all of the features or processes incorporated into the programmable daily reminder device 10. FIGS. 9–11 are flow charts showing how the basic version of the device 10 can be programmed using only the switch inputs 20, 22 to provide regularly scheduled alerts or reminders and showing how the alerts are executed. For this basic version, programming the regularly scheduled alerts is simplified because each scheduled alert will occur at the same time of day, on each subsequent day, when the alert was initially programmed. In other words, if the alert is programmed at 2:00 PM, the medical reminder device 10 will generate an output signal activating the primary audible output device 27 at 2:00 PM on each succeeding day, until the device is reprogrammed or subject to early activation in a manner that will be subsequently discussed in greater detail. This approach is especially suitable for reminding a user of regularly scheduled medications because it allows the user to initially program the medication event at the time when the user takes the initial dose of the particular medication or medications.

Figures 3, 6:
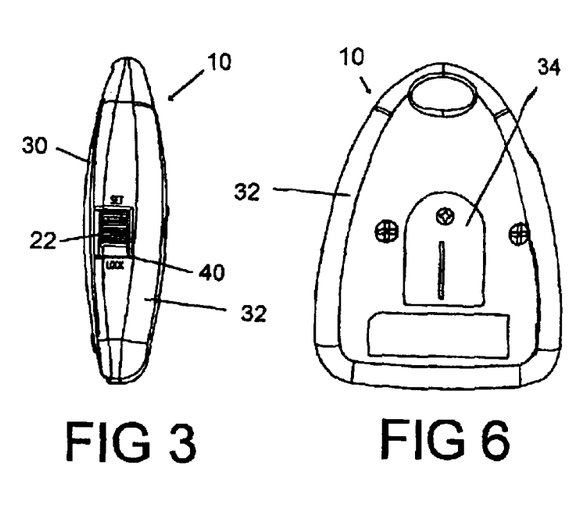
FIG. 3 is a right side view of the device of FIG. 1.
FIG. 6 is a rear view of the device of FIG. 1.
Figure 5:
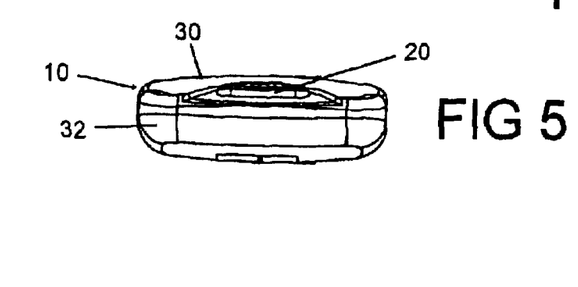
FIG. 5 is a bottom view of the device of FIG. 1.

FIG. 9 shows the steps for programming a first reminder or alert. This sequence starts with the reminder device 10 in a disarmed or locked state. Typically the device 10 will be in this state when the stable two position switch 24 is in the Lock or Disarmed state. The slide switch 24 is moved to the set or unlocked or Lock Off position as the first step in this sequence. If no further inputs are received within one minute, the device will timeout and the device will automatically return to the lock state, even thought the two position slide switch 24 physically remains in the Set or Lock Off position. To program a first event, the push button or primary programming switch 20 (SW1 as seen in FIGS. 6 and 7) should be pressed or closed prior to the expiration of the one minute timeout period. After two seconds, a distinct audible "programming" sound will be emitted by the audible output device 26. If the push button switch 20 is released, opened or turned off between two and four seconds, a first event will be programmed to occur at the same time of day on each subsequent day. By releasing the push button switch 20 at this point, the unit will enter the Armed State or State 1 as designed in FIG. 9.

If the operator fails to release the push button switch 20 and continues to press the primary programming switch 20 for at least four seconds, or two seconds after the programming sound is heard, the unit will be cleared, and all reminder alerts previously stored in memory will be cleared. As shown in FIG. 9, a disarming sound will be emitted after the push button switch is continuously activated for at least four seconds to inform the user that the unit's memory has been cleared. The unit will then return to the reminder Disarmed and Unlocked Timeouted State after a one minute timeout period. The unit will then be automatically locked to return to the initial Reminder Disarmed and Locked State. Alternatively, the user can lock the device before the one minute timeout by manually shifting the two position switch 22 to the Lock position. If the unit is automatically returned to the Reminder Disarmed and Locked State, the user will have to manually shift the two position switch 22 from the Set Position to the Lock Position and back to the Set Position before subsequent programming inputs.

This reminder unit 10 can also be programmed to alert the user at multiple times during each day. In the representative embodiment of this basic version, up to six reminders can be set each day. FIG. 10 shows the programming steps for setting additional alerts. As with the first alert, the subsequent alerts are programmed to occur at the same time of day on which the alert was originally entered. Before a second alert or event is entered, the device will be in the Reminder Armed and Locked State, shown at the upper right in FIG. 10. To program a new entry, the two position slide switch 22 is first shifted from its Lock Position to the Set Position, or the Lock Off action will be performed as shown in FIG. 10. The unit 10 will now be in the Reminder Armed and Unlocked State because at least one event or alert is resident in memory. The next step is to instruct the unit 10 to program a new entry by pressing or closing the push button switch 20 (PB On). At this point the unit 10 will respond with an audible sound, referred to in FIG. 10 as an "Entries Echo" sound. In the preferred embodiment, the user will hear a beep. With the push button switch 20 continuously held on for at least two seconds, the unit 10 will emit a programming sound, a two-tone sound in the preferred embodiment of this invention. If the push button switch is released between two and four seconds, the new entry or alert will be entered in memory, and an audible alert will be heard at the same time on each succeeding day. When the push button switch 20 is released and additional "Entries Echo" sound or beep will be heard indicating that the new event has been entered. However, if six entries are now in memory, a fault sound will be emitted. In either case the unit will return to the Reminder Armed and Unlocked State as shown on the left hand side of FIG. 10. The timeout procedure when multiple alerts have been programmed is substantially the same as for the single event programming shown in FIG. 9.

The alarm states for the medical reminder unit 10 are shown in FIG. 11. Once the reminder or unit 12 has been armed, the unit can enter the alarm state with the lock switch 22 in either the locked or unlocked state. The alarm state is identified as state 3 in FIG. 10. At the preset time of day, the reminder unit 10 will remind its user of a scheduled medical procedure by transmitting both an audible and a visual signal that can be detected by the user. As shown in the upper portion of FIG. 11, the Alarm State can be divided into "Noisy Period" during which both LED 28 and the audible output device 26 producing three tone signal will be activated and "Quiet Period" during which only LED 28 flashes. The Noisy period duration is always 30 seconds but the Quiet Period duration during the first hour of alarm is 9.5 minutes and after that is 14.5 minutes to conserve the battery. The exit from the Alarm state is possible only during the Noisy Period by pressing of pushbutton 20 switch. If the Pushbutton 20 switch is pressed during the Quiet period the Quiet Period is terminated and the unit enters into Noisy Period from which Alarm can be canceled using the Pushbutton switch 20 as described above.

The next alarm can also be pre-empted by the user prior to the next scheduled event. The user may wish to deactivate the device so that it will not sound and flash at the next scheduled time, because the user does not wish to be disturbed and/or because the user may have already taken his scheduled medication or the scheduled medical procedure has been completed. To pre-empt and scheduled reminder alarm, the user first moves the two position switch 22 from the Lock to the Set position, beginning from state 5 as shown in FIGS. 10 and 11. While the two position switch 22 is in the Set position, the user presses the push button switch 20 (PB On). While the push button switch remains in the ON state, the user then moves the two position switch 22 back to the Lock position. The reminder device will acknowledge preemption of the next Alarm by instantly entering into one short cycle (only 15 sec ) of the Noisy Period of the Alarm. If during this period the pushbutton switch 20 is pressed, the next Alarm will be pre-empted. Otherwise the Alarm will timeout, and the operation will not only be ignored, but the previous preempting of the next Alarm will be canceled.

If the user has thus pre-empted the next alarm as shown in the lower portion of FIG. 11, the alarm will not sound at the next scheduled event, but will sound normally at all subsequent times. Based on these flow charts, one of ordinary skill in the art could program the software and/or firmware based using the standard instruction set and user manual for specific microcontroller employed in the specific reminder device.

The representative embodiment of this basic medical reminder 10 device described herein can be used by an individual in a number of different ways by manipulating only two simple switches, either individually or in unison. To set a reminder alert at a time of day that the user wishes to take medication or perform some other scheduled task, the user first moves the slide or two position switch 22 on the side of the unit to its Set position. Then the user presses the push button switch 20 on the front of the unit. The reminder device will acknowledge the pushbutton pressing by releasing as many beeps as is number of Alerts already programmed. If this is the first Alert being programmed then none. The user will continue to hold push button switch 20 until he/she hears a two-tone sound, whereupon the user releases the push button switch 20. The unit responds by releasing as many beeps as is number of events already programmed, including the last event. Note that in order to set the event, the user has simultaneously activated two separate switches. The unit cannot be set by inadvertent actuation of the single push button switch 20. At this point the user will move the two position switch back to it Lock position. The unit will then sound an alert with an audible beeping sound and a blinking light at this same time of each subsequent day until this event or reminder is deactivated. As explained in discussing the flow charts, the device will automatically return to a Lock state after a specified time, even if the user should forget to move the slide switch 22 to the Lock position. In this case the reminder will emit a long low tone every time the pushbutton is pressed to remind the user to lock the reminder.

The user can also program additional events. In the representative embodiment, the user can program up to six events, although other devices could include more than six events. At a second time of the day, when the user wishes to take a second medication or perform a second medical procedure, the user will again move the two position switch 22 to the Set position. If the user had forgotten to move the two position or slide switch 22 to the Lock position after the last use of the device, the user will now have to first move the switch to its Lock position and then back to its Set position because the device would ignore the pushbutton otherwise and it will emit a long low tone sound instead. After the unit is placed in its Set position by manipulation of switch 22, the user will again press and hold the push button switch 20 until the beep is followed by a two-tone sound. The user then releases the push button switch 20 and the device confirms this additional programming sep by emitting a second beep. The use should then return the slide switch 22 to its Lock position. Now the device will sound an audible alert and the LED will flash at both times of day.

When the unit 10 sounds an alarm to remind the user of each scheduled event, the user will then press the push button switch 20, and the unit will sound a number of beeps corresponding to the number of daily reminder events that have been programmed into the microcontroller memory. If the user does not acknowledge the scheduled reminder alarm when it sounds by pressing the push button, the light will continue to blink indefinitely and the alarm will sound the alert for thirty seconds every ten minutes for the first hour. The alarm will sound every fifteen minutes after the first hour. The unit will continue to operate in this manner until the user presses the push button switch 20, when the unit will again sound the alarm. The user should then press the push button switch 20 to again acknowledge the event.

The user may also activate the reminder event before its scheduled time. The slide switch 22 is first moved to its Set position and the user will then press and hold the push button switch 20. While holding the push button switch down, the user will move the slide switch 22 back to its Lock position and then release the push button switch 20. The unit will then sound the alert and the user should then acknowledge the alert by again pressing the push button switch 20. At this point the reminder unit 10 will skip the regular timing of the next event and will thereafter revert to its original settings. This early activation feature can be employed on a reminder device that is not be programmed in the simple manner discussed with reference to the basic representative embodiment. For example, this early activation feature can be used on a remotely programming reminder device that could be programmed or reprogrammed by use of an on-site computer or by a computer connected by an Internet or telecommunications line communicating with the microcontroller.

The user can clear all previously set reminder alerts by first moving the slide or two position switch 22 to the Set position. Next the user should press and hold the push button switch 20 until the user first hears beeps, then a two-tone sound, and then a second two-tone sound. When the user then releases the push button switch 20, all previously scheduled events will be deleted from memory and the unit will be cleared. The slide switch should then be moved back to the Lock position. The unit can then be reprogrammed as before.

Figure 12:
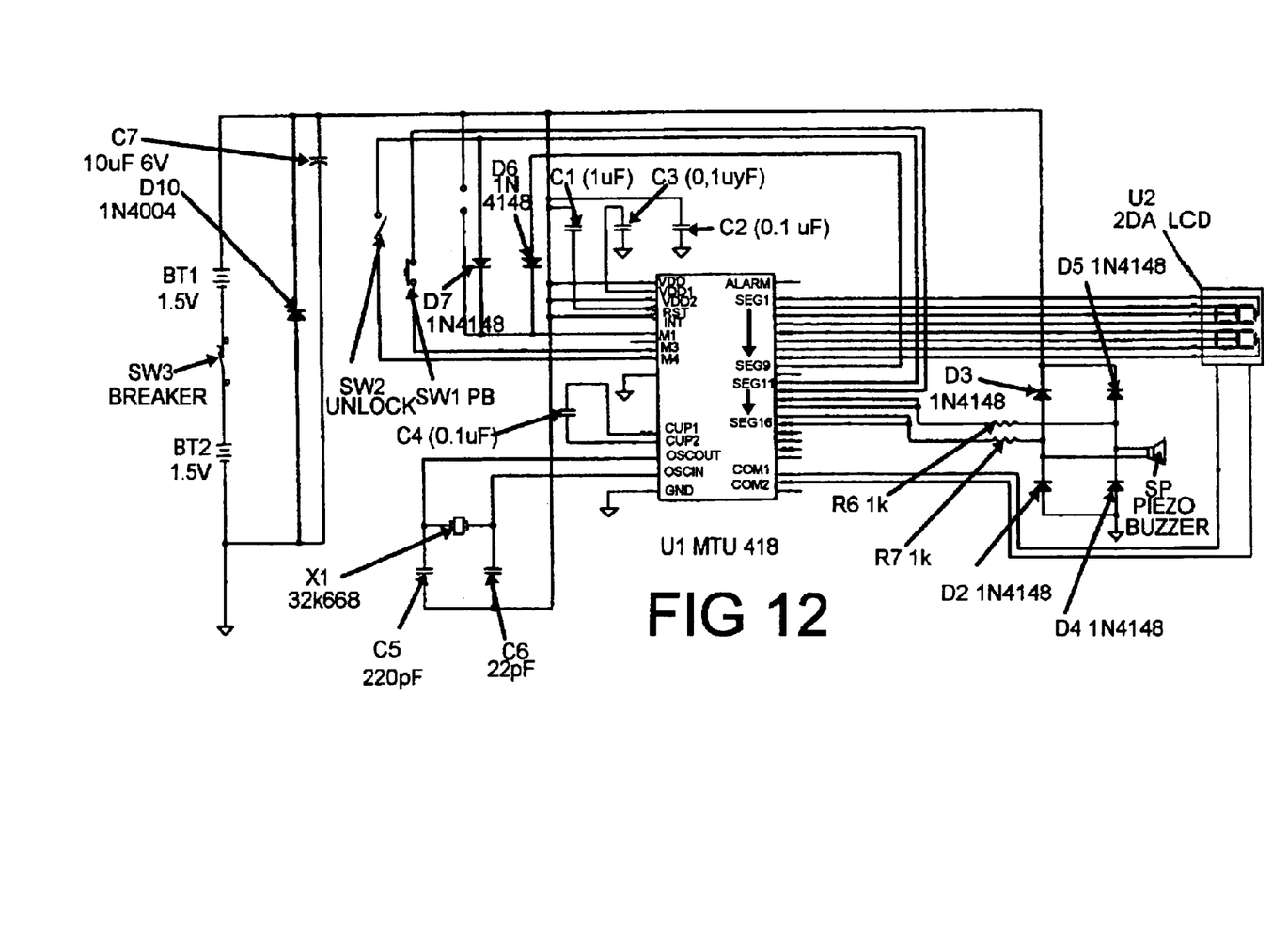
FIG. 12 is a schematic showing the manner in which an alphanumeric LCD output could be employed in a reminder device.

Significant aspects of this invention can be employed in alternative embodiments. FIG. 12 shows the manner in which information can be output on an LCD display. COM1 And COM2 are microcontroller output pins for the LCD panel common plate. SEG1 through SEG9 are microcontroller output pins for the LCD panel segments. The LCD panel is useful for 48 hour, 7 day and 30 day single alarm units where the two digits of the LCD shown rounded number days remaining to Alarm. The LCD is designed to replace the LED. During the Alarm the LCD displays two flashing zeros.

Figures 13, 14:
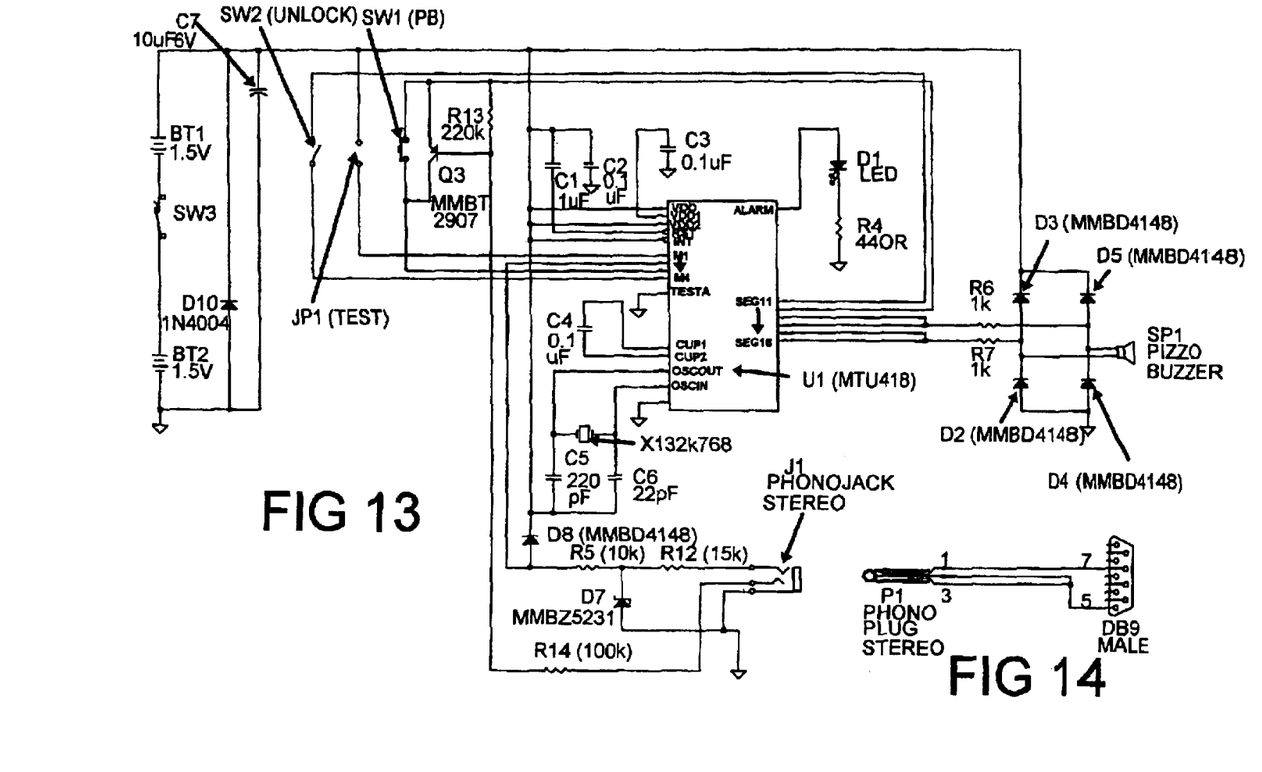
FIG. 13 is a schematic showing the manner in which a reminder device can be programmed by a external computer.
FIG. 14 is a schematic of the input cable assembly used with the reminder vice shown in FIG. 13.

FIG. 13 shows a schematic for an alternative embodiment that can be remotely programmed by a computer accessible through a stereo phone jack J1, through which data may be serially input to input port M2. Switch SW1 is connected to input port M3 while switch SW2 is connected to input port M4. In this version, the microcontroller is programmed so that the functions of switches SW1 and SW2 differs from their function in the embodiment of FIGS. 1–11. The push button switch SW1 retains its primary execution function of acknowledging an alarm signal generated by a preset scheduled reminder, and therefore of deactivating the alarm until the next scheduled reminder. The push button switch will acknowledge the alarm either at it normal time or during the delay intervals in the same manner as with the basic version of FIGS. 1–11. The slide switch SW2 has only two positions, NORM (Normal) and ACT. Switch SW2 is used only for early activation and should typically be left in its NORM position. To activate a reminder event before its scheduled time, the switch SW2 is first moved to its ACT position. With switch SW2 in the ACT position, the push button switch SW1 is then pressed and held. While switch SW1 is held down, slide switch SW2 is returned to its NORM position. The momentary push button switch SW1 is then released, and the reminder reacts on the above operation by sounding of a short alarm (one alarm cycle). If this alarm is then acknowledged and silenced again by pressing the momentary push button switch SW1, then the reminder device will skip the next scheduled event, after which the device will function according to its regular schedule. If the alarm is not acknowledged then the next scheduled event will not be suppressed even if it has been cancelled before.

FIG. 14 shows the pin assignments of a signal cable that can be used to connect the reminder device to a RS232 serial port on a computer for inputting reminder events into the microcontroller memory. In the preferred embodiment, the reminder device will be powered by batteries with a voltage of between 1.3V to 3V. In addition, the miniature stereo phone jack is used as a programming cable connector. Neither Voltage level nor connector are compatible with RS232, but an input circuit and custom cable are used to provide the appropriate interface to the host computer. An application program can be stored in a host computer's memory and will permit reminder events to be designated and input into a reminder device connected to the computer by the cable. In a preferred embodiment, up to either separate daily events can be programmed. The computer program will also permit removal of reminder events. After the reminder device has been programmed in this manner, it can be disconnected from the computer and the cable, and can then function in a normal manner.

One of ordinary skill in the art could readily modify these embodiments by employing equivalent means. Therefore it should be understood that the preferred embodiment disclosed herein is representative only and the invention is defined by the following claims which are applicable to this representative embodiment and alternate embodiments that would be apparent to one of ordinary skill in the art.

We claim:

1. A programmable reminder device comprising means for providing at least one daily reminder and including:
   a microcontroller including timing means;
   a signaling component responsive to the microcontroller to emit a signal detectable by the operator of the reminder device;
   a first momentary input; and
   a second stable input;
   wherein the first and second input's comprise first and second switch inputs, simultaneous activation of the first and second inputs setting the microcontroller to activate the signaling component daily at the same time that the two switch inputs were originally simultaneously activated to simplify programming of periodic scheduled events;
   the microcontroller being configured so that simultaneous actuation of both inputs sets the microcontroller to activate the signaling component daily at a specified time, so that the microcontroller cannot be inadvertently set by activation of a single input.

2. The programmable reminder device of claim 1, wherein the first switch input comprises a push button switch actuated only during exertion of an external force.

3. The programmable reminder device of claim 2 wherein the second switch input comprises a two position switch shiftable between a set and a lock position, the two position switch remaining in either the set or lock position until an external force is applied to shift the two position switch.

4. A programmable medication reminder device comprising:
   a microcontroller including clock means and a memory;
   a first input switch and a second input switch;
   an output device detectable by a user of the programmable device, the output device being responsive to the microcontroller;
   the first input switch and the second input switch being connected to the microcontroller so that when the first input switch is activated while the second input switch is in an activated state at a specific time of day, that time of day will be stored in the memory as an event and the microcontroller will send a signal to activate the output device at the same time on succeeding days; and
   the first input switch and the second input switch being connected to the microcontroller so that when the second input switch is deactivated, while the first input switch is in an activated position, the microcontroller will not activate the output device upon a next event.

5. The programmable medication reminder device of claim 4 wherein when the second input switch is deactivated state, while the first input switch is in an activated position, the microcontroller will not activate the output device only upon the next event, and the microcontroller will activate the output device upon subsequent events, including a similarly timed event on subsequent days.

6. The programmable medication reminder device of claim 4 wherein the multiple specific times of day can be programmed into the memory by deactivation of the first input switch while the second input switch is in an activated state.

7. The programmable medication reminder device of claim 4 wherein the output device is activated at the specific time of day when the second input switch is in a deactivated state.

8. The programmable medication reminder device of claim 4 wherein the second input switch is moved to a deactivated state either by manipulation of the second input switch after activation of the first input switch or by elapse of a specified interval after activation of the first input switch.

9. The programmable medication reminder device of claim 4 wherein the first input switch is a push button switch and the second input switch is a two position switch including a stable activated position and a stable deactivated position, application of an external force being required to move the two position switch between the activated and deactivated positions.

10. The programmable medication reminder device of claim 9 wherein the two position switch comprises a slide switch.

11. The programmable medication reminder device of claim 4 herein the output device comprises an audible device.

12. The programmable medication reminder device of claim 4 wherein the first input switch is connected to the microcontroller so that upon activation of the output device, activation of the first input switch, with the second input switch in the deactivated state, signals the microcontroller to deactivate the output device and any periodic reminders of a most recent event signaled by the output device.

* * * * *